United States Patent [19]

Johnson

[11] 4,439,364

[45] Mar. 27, 1984

[54] PROCESS FOR PREPARING ANTIHYPERTENSIVE 1-SUBSTITUTED CYCLIC LACTAM-2-CARBOXYLIC ACIDS AND THEIR DERIVATIVES

[75] Inventor: Alexander L. Johnson, Wilmington, Del.

[73] Assignee: E. I. Du Pont de Nemours & Company, Wilmington, Del.

[21] Appl. No.: 413,786

[22] Filed: Sep. 1, 1982

[51] Int. Cl.³ .......................................... C07D 223/10
[52] U.S. Cl. ........................... 260/239.3 R; 546/221; 546/243; 548/533
[58] Field of Search ................. 260/239.3 R; 546/221, 546/243; 548/533

[56] References Cited

U.S. PATENT DOCUMENTS 4,296,110 10/1981 Johnson ............................ 424/244

FOREIGN PATENT DOCUMENTS 12401 6/1980 European Pat. Off. ............ 424/274

OTHER PUBLICATIONS

W. J. Greenlee, *Tetrahedron Letters,* vol. 23, 3995–3998, (1982), Preparation of Substituted N–Carboxymethyl Dipeptides.

*Primary Examiner*—Robert T. Bond

[57] ABSTRACT

Certain antihypertensive 1-substituted cyclic lactam-2-carboxylic acids and their derivatives are prepared by reacting an ester of the formula

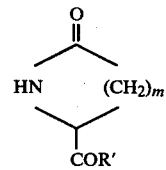

with a suitable derivative of the formula

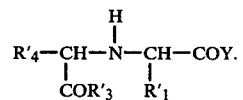

4 Claims, No Drawings

PROCESS FOR PREPARING ANTIHYPERTENSIVE 1-SUBSTITUTED CYCLIC LACTAM-2-CARBOXYLIC ACIDS AND THEIR DERIVATIVES

BACKGROUND OF THE INVENTION

Compounds of Formula I are disclosed as antihypertensive agents in U.S. Pat. No. 4,296,110, issued Oct. 20, 1981, to A. L. Johnson.

$$R_4-CH(COR_3)-N(R_2)-CH(R_1)-CON\underset{O}{\overset{COR}{\diagup}}\hspace{-2pt}\diagdown(CH_2)_m \quad (I)$$

where

R and $R_3$ are independently OH, $C_1$-$C_4$ alkoxy or $C_6H_5CH_2O$;

$R_1$ is H, $CH_3$, $C_2H_5$, $CF_3$, isobutyl, isoamyl, $-(CH_2)_n NHR_5$ or $$-(CH_2)_p NH\overset{NH}{\overset{\|}{C}}-NH_2;$$

$R_2$ is H or $CH_3$;
$R_4$ is $C_1$-$C_{10}$ alkyl; $-(CH_2)_q C_6H_5$ or $-(CH_2)_r NH_2$;
$R_5$ is H or $C_1$-$C_4$ alkyl;
m is 2, 3 or 4;
n is an integer from 1–6;
p is an integer from 1–6;
q is an integer from 0–6; and
r is an integer from 1–6;
and pharmaceutically acceptable salts thereof.

The same patent also discloses a method of preparing compounds of Formula I by coupling the alkali metal salt of an ester of the formula $$HN\underset{COR'}{\diagdown}\hspace{-2pt}\diagup(CH_2)_m$$

where R' is $C_1$-$C_4$ alkoxy or benzyloxy, with a suitable derivative of the formula $$R'_4-CH(COR'_3)-N(R'_2)-CH(R'_1)-COY$$

in which
Y is ethoxycarbonyloxy, methoxycarbonyloxy, N-oxysuccinimidyl or 4-nitrophenoxy;
$R_1'$ is H, $CH_3$, $C_2H_5$, $CF_3$, isobutyl, isoamyl, $(CH_2)_n NR_5 COOCH_2 C_6 H_5$ or $(CH_2)_p NH-C(=NH)NHNO_2$;
$R_2'$ is $CH_3$, carbobenzyloxy or tert-butoxycarbonyl;
$R_3'$ is $C_1$-$C_4$ alkoxy or benzyloxy;
$R_4'$ is $C_1$-$C_{10}$ alkyl, $-(CH_2)_q C_6 H_5$, $-(CH_2)_r NH-$ or $COOCH_2 C_6 H_5$; and
$R_5$, m, n, p, q and r are as previously defined.

The standard protective groups are removed to yield the compounds of Formula I.

SUMMARY OF THE INVENTION

An improved process for preparing the compounds of Formula I has now been found. An anion of the formula $$^{\ominus}N\underset{O}{\overset{COR'}{\diagup}}\hspace{-2pt}\diagdown(CH_2)_m \quad II$$

where R' is OX, $C_1$-$C_4$ alkoxy or benzyloxy, is coupled with an amino-diacid of the formula $$R'_4-CH(COR'_3)-\overset{H}{N}-CH(R'_1)-COY \quad III$$

where
$R_1'$ is H, $CH_3$, $C_2H_5$, $CF_3$, isobutyl, isoamyl, $-(CH_2)_n NR_5-X^1$ or $-(CH_2)_p N-C(=NH)NH-X^2$;
$R_3'$ is $OX^3$, $C_1$-$C_4$ alkoxy or benzyloxy;
$R_4'$ is $C_1$-$C_{10}$ alkyl, $-(CH_2)_q C_6 H_5$ or $-(CH_2)_r NH-X^4$;
$R_5$ is H or $C_1$-$C_4$ alkyl;
m is 2, 3 or 4;
n is an integer from 1–6;
p is an integer from 1–6;
q is an integer from 0–6;
r is an integer from 1–6;
X, $X^1$, $X^2$, $X^3$ and $X^4$ are protective groups; and
Y is a carboxyl-activating group;
to prepare an intermediate of the formula $$R'_4-CH(COR'_3)-N(R_2)-CH(R'_1)-CON\underset{O}{\overset{COR'}{\diagup}}\hspace{-2pt}\diagdown(CH_2)_m$$

where $R_2$ is H and all other substituents are as defined above.

The various protective groups, X–$X^4$, are removed from the product Ia to yield the desired antihypertensive compounds of Formula I where $R_2=H$. Compounds of Formula I where $R_2=CH_3$ can be made with the addition of a methylation step, preferably before the removal of such protective groups as may be desired.

The unexpected finding that the coupling reaction of this invention can be used directly to prepare compounds of Formula Ia where $R_2=H$ is a particularly useful discovery since the synthesis of these compounds is thereby shortened by two steps, N-protection and N-deprotection.

DETAILED DESCRIPTION OF THE INVENTION

The anion of Formula II used in the process of this invention can be generated by converting the appropriate ester into an alkali metal salt using a basic reagent such as sodium hydride, potassium hydride, lithium hydride, lithium di-isopropylamide, n-butyl lithium and potassium t-butoxide. The use of sodium hydride to generate the sodium salt of II is preferred for reason of convenience. Suitable inert solvents for the salt generation and the subsequent coupling reaction include aprotic solvents such as, but not limited to, toluene, ether, dioxane, tetrahydrofuran, 1,2-dimethoxyethane, N,N-dimethylformamide and dimethylsulfoxide. The salt formation and the coupling reaction may be carried out at a temperature of about −10° to about 50° C., preferably at about 0° to 25° C., and more preferably at about room temperature, i.e., 20 to 25° C.

The amino and carboxy groups in the anion II and aminodiacid III are protected by any standard protective groups. One skilled in the art would be familiar with such groups and would be able to select the appropriate protective groups to use in the process of this invention. Examples of protective groups include benzyloxycarbonyl, benzyl, nitro, tert-butyl and tert-butyloxycarbonyl groups. For further information regarding protective groups, see Bodansky, Klousner and Ondetti, "Peptide Synthesis", Second Edition, 1976, Wiley, N.Y., the disclosure of which is herein incorporated by reference.

The carboxyl-activating groups, Y, serve to activate the acid III toward coupling. Groups which would be suitable would also be known to one skilled in the art. Examples of such groups include ethoxycarbonyloxy, methoxycarbonyloxy, N-succinimidyloxy and 4-nitrophenoxy, with N-succinimidyloxy being the preferred group. For further information regarding carboxyl-activating groups, see Bodansky et al., cited above.

The aforementioned reference also describes standard methods for removal of the protective groups. For example, protective groups such as the benzyloxycarbonyl, benzyl and nitro groups can be removed by hydrogenation in the presence of palladium-on-charcoal, especially in ethanolic hydrogen chloride. The tert-butyl or tert-butoxycarbonyl groups can be removed by treatment with trifluoroacetic acid. Again, one skilled in the art would be familiar with the appropriate methods for protective group removal.

Compounds of Formula I where $R_2=CH_3$ can be prepared by methylating the product of the coupling reaction, preferably before removal of the protective groups. Methylation of Ia can be accomplished by methods well known in the art, for example, reaction with methyl iodide in a suitable solvent such as methanol, ethanol, acetonitrile or dimethylformamide, optionally in the presence of a base such as sodium carbonate or bicarbonate or potassium carbonate or bicarbonate. Another methylation method involves reaction of Ia with a mixture of formic acid and formaldehyde.

The ester (II) and amino-diacid (III) used as starting materials in the process of this invention can be prepared as described in U.S. Pat. No. 4,296,110, the disclosure of which is hereby incorporated by reference.

The process of this invention is illustrated in the following examples in which temperatures, reported in degrees Centigrade, are uncorrected, and percentages are by weight.

EXAMPLE 1

Preparation of [N-(1S-Ethoxycarbonyl-3-phenylpropyl)-RS-alanyl]-S-pyroglutamic Acid, t-Butyl Ester A. S-(+)-2-Amino-4-phenylbutyric Acid, Ethyl Ester, Hydrochloride

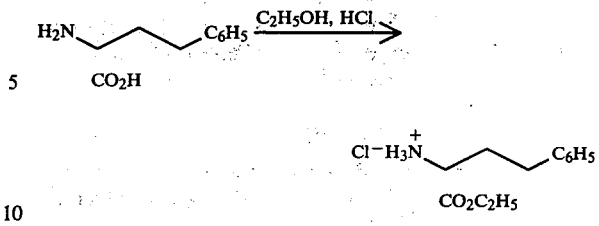

A mixture of S-(+)-2-amino-4-phenylbutyric acid, $[\alpha]_D^{25°} +44.6°$ (1N HCl), (2.0 g, 11.16 mmole) an absolute ethanol (50 ml) was treated with dry hydrogen chloride at 25°. The solid dissolved within 5–10 minutes, after which the mixture was cooled to 0° and saturated with dry hydrogen chloride. The mixture was left at 25° overnight, stirred at reflux for 1 hour, and then evaporated to leave a colorless solid residue of the ethyl ester hydrochloride (2.63 g, 10.09 mmole, 90%).

Repetition on 5.9- and 10-gram scales gave yields of 96% and 72% respectively of S-(+)-2-amino-4-phenylbutyric acid, ethyl ester, hydrochloride, m.p. 150°–151°; $[\alpha]_D^{25°} +40.0°$ (EtOH).

B. N-(1S-Ethoxycarbonyl-3-phenylpropyl)-RS-alanine

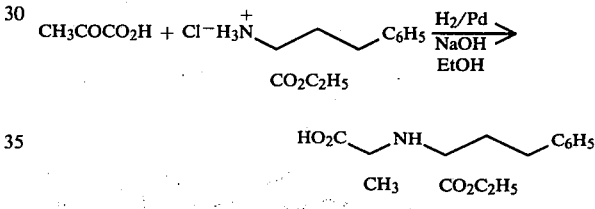

A mixture of S-(+)-2-amino-4-phenylbutyric acid, ethyl ester, hydrochloride (2.33 g, 8.94 mmole), pyruvic acid (1.76 g, 20 mmole), 5% palladium-on-carbon (0.5 g), sodium hydroxide (0.6 g, 15 mmole, predissolved) and ethanol (200 ml) was shaken at 250° under a pressure of 40 psig (280 kPa, gauge) hydrogen in Parr shaker apparatus. The uptake of hydrogen was 18 psig (∼18 mmole) over 23 hours.

The catalyst was filtered through a bed of Celite and the filtrate was evaporated to leave an essentially quantitative yield of the desired product as a colorless solid. The crude sample was triturated with ether, filtered, and dried at 25°/0.1 mm (13 Pa) to provide 2.14 g (7.66 mmole, 86%) of colorless solid, m.p. 132°–134°. The material prepared by this simple procedure contains entrained sodium chloride, but is satisfactory for further work.

Anal. Calcd. for $C_{15}H_{21}NO_4HCl$: C, 57.05; H, 7.02; N, 4.14; Cl, 11.23. Found: 57.71, 57.79; H, 6.42, 6.94; N, 4.08, 4.44; Cl, 4.25.

Repetition of the experiment on a 5–8 g scale gave yields of 68–88%. Material recrystallized from acetone has $[\alpha]_D^{25°} +16.9°$ (EtOH).

C. N-(1S-Ethoxycarbonyl-3-phenylpropyl)-RS-alanine, N-Succinimidyl Ester (III: Y=N-succinimidyloxy; $R_1'=CH_3$; $R_3'=EtO$; $R_4'=-(CH_2)_2C_6H_5$).

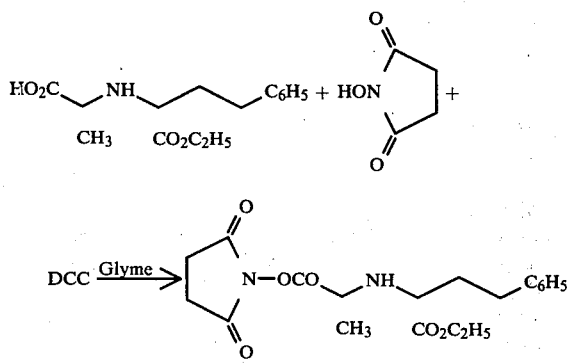

A mixture of N-(1S-Ethoxycarbonyl-3-phenyl-propyl)-RS-alanine (0.50 g, 1.79 mmole), glyme (5 ml), N-hydroxysuccinimide (0.2072 g, 1.80 mmole) and dicyclohexylcarbodiimide (DCC) (0.3714 g, 1.80 mmole) was stirred at 5° overnight, then filtered through Celite filter aid. The filtrate was diluted with CHCl$_3$ (25 ml) and extracted with 10% Na$_2$CO$_3$ (3×10 ml). The chloroform extract was dried and evaporated to leave 0.58 g (1.54 mmole, 86%) of crude N-succinimidyl ester as a colorless sirup.

Repetition of the above experiment on scales of 10-13 mmole gave essentially quantitative conversion to the N-succinimidyl ester as measured by dicyclohexylurea production and yield of crude ester. This intermediate is recognized by its infrared bands at 1820 and 1790 cm$^{-1}$, and by an intense signal at 2.83 ppm in the NMR spectrum.

D. [N-(1S-Ethoxycarbonyl-3-phenylpropyl)-RS-alanyl]-pyroglutamic Acid, t-Butyl Ester (I: R=t-BuO; m=2; R$_1$=Me; R$_{2=H}$; R$_3$=EtO; R$_4$=—(CH$_2$)$_2$C$_6$H$_5$)

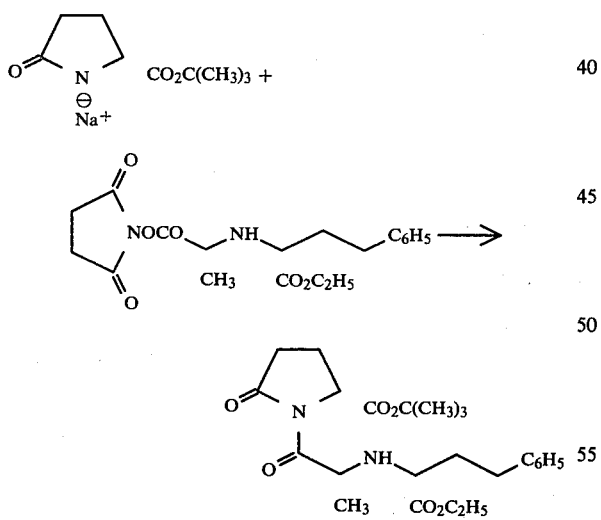

The sodium salt of t-butyl pyroglutamate was prepared in toluene (5 ml), using 60% sodium hydride (64.0 mg, 1.60 mmole) and t-butyl pyroglutamate (296.4 mg, 1.60 mmole), and reacted with the N-succinimidyl ester from Example 1(C) above (580 mg, 1.54 mmole) overnight at 25°. The mixture was extracted with water (3×10 ml), the organic layer was dried and evaporated leaving the sirupy crude product which was flash chromatographed (50 g silica gel; 3:1 CH$_2$Cl$_2$: EtOAc eluant) to provide 392.7 mg (0.88 mmole, 55%) of pure material which was dried at 50°/0.1 mm for analysis. [N-(1S-Ethoxycarbonyl-3-phenylpropyl)-RS-alanyl]-S-pyroglutamic Acid, t-butyl ester, is characterized as a colorless oil. IR(CHCl$_3$): 1740 cm$^{-1}$; [α]$_D^{25°}$ −54.5° (EtOH).

Anal. Calcd. for C$_{24}$H$_{34}$N$_2$O$_6$: C, 64.55; H, 7.67; N, 6.27. Found: C, 64.25, 64.58; H, 7.73, 7.74; N, 6.13, 6.05.

Repetition of this procedure on a four-gram scale provided the diester in 59% yield.

EXAMPLE 2

[N-(1S-Ethoxycarbonyl-3-phenylpropyl)-RS-alanyl]-S-pyroglutamic Acid, Trifluoroacetic Acid Salt (I: R=OH; m=2; R$_1$=Me; R$_2$=H; R$_3$=Eto; R$_4$=—(CH$_2$)$_2$C$_6$H$_5$; • CF$_3$CO$_2$H)

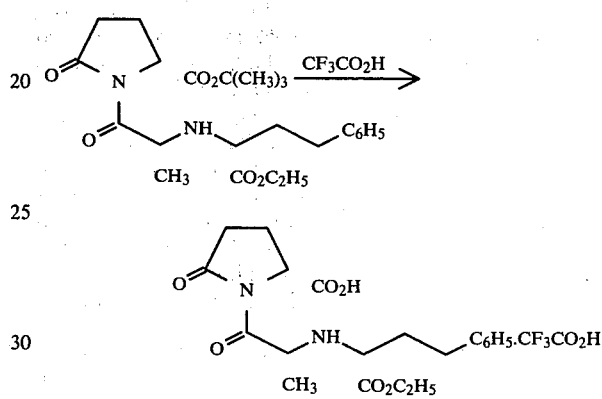

A mixture of the t-butyl ester from Example 1(D) (1.82 g, 4.08 mmole) and trifluoroacetic acid (50 ml) was stirred at 25° for 1 hour. The solvent was evaporated at 25° to leave a sirup which no longer exhibited the NMR signal (delta 1.50) characteristic of the t-butyl group of the starting material. IR(film): 1750 cm$^{-1}$; $^{19}$F NMR (CDCl$_3$/F-11) delta −76.51 ppm (s; CF$_3$CO$_2^-$).

EXAMPLE 3

Preparation of [N-(1R-Ethoxycarbonyl-3-phenylpropyl)-RS-alanyl]-S-pyroglutamic Acid, t-Butyl Ester, and Separation of Diastereomers A. R-2-Amino-4-phenylbutyric Acid, Ethyl Ester, Hydrochloride

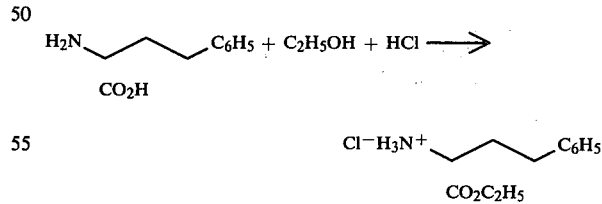

A sample of R(−)-2-amino-4-phenylbutyric acid, [α]$_D^{25°}$ −44.1° (1N HCl), (24.54 g, 0.137 mole) was converted to its ethyl ester hydrochloride using the procedure of Example 3. The yield of product was 30.59 g (0.126 mmole, 92%). A one gram sample was recrystallized from a mixture of ethanol (5 ml) and ether (20 ml) with activated charcoal treatment, m.p. 153°-154° (dried at 25°/0.1 mm over P$_2$O$_5$). The purified ethyl ester hydrochloride has IR(KBr): 3420, 1742, 1580 cm$^{-1}$; [α]$_D^{25°}$ −40.2° (EtOH).

Anal. Calcd. for $C_{12}H_{18}NO_2Cl$: C, 59.13; H, 7.44; N, 5.75. Found: C, 59.24, 58.96; H, 7.43, 7.48; N, 5.72, 5.78.

B. N-(1R-Ethoxycarbonyl-3-phenylpropyl)-RS-alanine

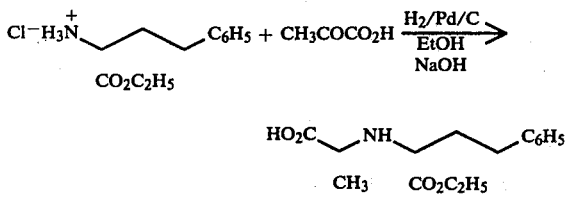

(1) A mixture of R-2-amino-4-phenylbutyric acid, ethyl ester, hydrochloride, from Example 3(A) above (10.0 g, 0.042 mole), ethanol (300 ml), predissolved sodium hydroxide (2.62 g, 0.065 mole), pyruvic acid (10.30 g, 0.117 mole) and 5% palladium-on-carbon (1 g) was hydrogenated in a Parr shaker for 22 hours at 25° C. The product obtained by filtration, evaporation of the filtrate and trituration with ether did not crystallize, but contained N-(1R-ethoxycarbonyl-3-phenylpropyl)-RS-alanine by NMR. It was freed from the lactic acid produced in the hydrogenation by ionexchange chromatography on AG 50 W-X2 100–200 mesh resin using 2×100 ml of 50% aqueous ethanol, 4×100 ml of 25% ethanol and 11×200 ml of 2% pyridine to elute the components of the mixture. The desired product was contained in fractions 10–17, recovery 6.80 g. A similar experiment gave 4.98 g of material; total recovery from the 20.0 g of starting material was 11.78 g (42.2 mmole, 54%) of crystalline product.

(2) The above experiment was repeated using fresh pyruvic acid (7.78 g, 0.088 mole), the quantities of other materials being the same as above. The crude product (6.00 g, 0.0215 mole, 55%) crystallized directly upon trituration with ether, as previously observed when starting with S-(+)-2-amino-4-phenylbutyric acid.

Two recrystallizations of 0.5 g of product from (1) above from acetone (10 ml) with Darco treatment and addition of hexane to the filtrate gave N-(1R-ethoxycarbonyl-3-phenylpropyl)-RS-alanine as a colorless solid, m.p. 148°–149°. IR (KBr): 3440, 1748, 1620 cm$^{-1}$; $[\alpha]_D^{25°}$ −12.8° (EtOH).

Anal. Calcd. for $C_{15}H_{21}NO_4$: C, 64.50; H, 7.58; N, 5.01. Found: C, 64.3, 64.5; H, 7.6, 7.6; N, 5.2, 5.4.

MS: $C_{15}H_{21}NO_4$ requires m/z 279.1470; found, 279.1511.

C. N-(1R-Ethoxycarbonyl-3-phenylpropyl)-RS-alanine, N-succinimidyl Ester (III: Y=N-succinimidyloxy; $R_1'$=CH$_3$, $R_3'$=Eto; $R_4'$=—(CH$_2$)$_2$C$_6$H$_5$)

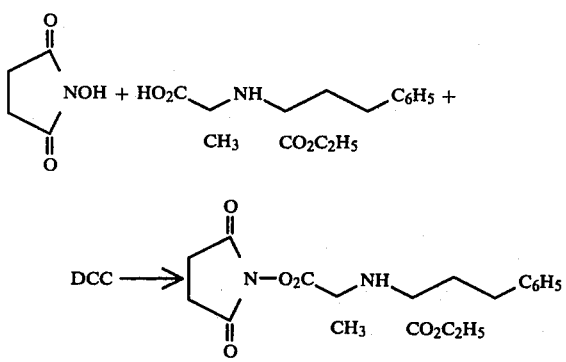

A mixture of N-(1R-ethoxycarbonyl-3-phenylpropyl)-RS-alanine (9.37 g, 33.5 mmole), glyme (150 ml), chloroform (150 ml), N-hydroxysuccinimide (3.85 g, 33.5 mmole) and dicyclohexylcarbodiimide (6.91 g, 33.5 mmole) was stirred overnight. Dicyclohexyl urea (7.60 g, 33.9 mmole, 100%) was removed by filtration to give 11.68 g (31.0 mmole, 93%) of N-succinimidyl ester. The N-succinimidyl ester was identified by IR and NMR spectra. Repetition of the experiment on a 6-g scale gave 8.18 g (100%) of N-succinimidyl ester which was dried at 40°/0.1 mm (13 Pa). N-(1R-Ethoxycarbonyl-3-phenylpropyl)-RS-alanine, N-succinimidyl ester, is characterized by IR(CHCl$_3$): 1812, 1785, 1740 cm$^{-1}$; $[\alpha]_D^{25°}$ +28.4° (THF).

Anal. Calcd. for $C_{19}H_{24}N_2O_6$: C, 60.63; H, 6.43; N, 7.44. Found: C, 61.02, 61.25; H, 6.44, 6.74; N, 7.56, 7.46.

MS: $C_{19}H_{24}N_2O_6$ requires m/z 376.1634; found, 376.1597.

D. [N-(1R-Ethoxycarbonyl-3-phenylpropyl)-RS-alanyl]-S-pyroglutamic Acid, t-Butyl Ester (I: R=t-BuO; m=2, $R_1$=Me, $R_2$=H, $R_3$=EtO; $R_4$=—(CH$_2$)$_2$C$_6$H$_5$

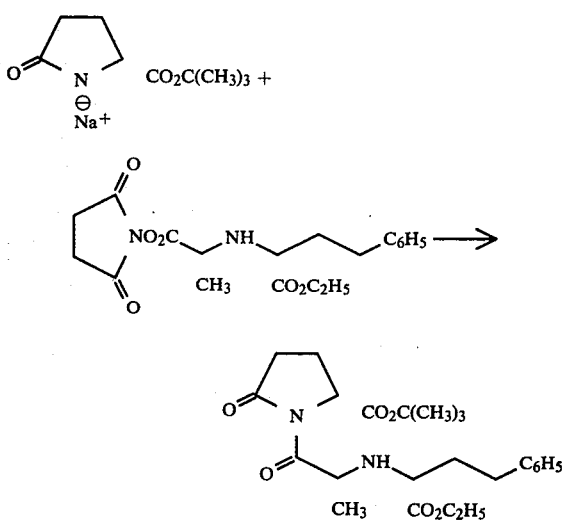

The procedure given in Example 1(D) was used to convert 6.19 g (33.4 mmole) of t-butyl S-pyroglutamate and 11.68 g (31.0 mmole) of the N-succinimidyl ester from 3(C) above into 11.51 g (25.7 mmole, 83%) of the crude title compound which was shown to be a mixture of the two possible diastereomers by chromatography. By TLC (silica gel; 3:1 CH$_2$Cl$_2$:EtOAc) diastereomer A had R$_f$0.75 and diastereomer B, R$_f$0.43. The two diastereomers were separated by flash chromatography on silica gel in the same solvent system to give 2.46 g (30%) of diastereomer A and 5.68 g (70%) of diastereomer B. They are distinguished from one another by their chromatographic behavior, optical rotation and 360 MHz NMR spectra in the delta 4.6, 4.1 and 1.3 regions. Chromatographic purification gives satisfactory material, and each diastereomer was dried at 50°/0.1 mm for analysis.

Diastereomer A is a colorless oil, NMR (CDCl$_3$): delta 4.611 (AB, each d J=10, each d J=3), 4.517 (q, J=7, NCH protons), 4.117 (m), OCH$_2$, 1.317 (d, J=7, alanine-CH$_3$) and 1.254 (t, J=7, ethyl-CH$_3$).

Anal. Calcd. for $C_{24}H_{34}N_2O_6$: C, 64.55; H, 7.67; N, 6.27. Found: C, 64.69, 64.75; H, 7.78, 7.77; N, 6.25, 6.35.

MS: $C_{24}H_{34}N_2O_6$ requires m/z 446.2417; found, 446.2438.

Diastereomer B is also a colorless oil, NMR (CDCl$_3$): delta 4.591 (AB, each d J=9, each d J=3), 4.569 (q, J=7, 2×NCH protons), 4.177 (q, J=7, each d J=2, OCH$_2$), 1.304 (d, J=7, alanine-CH$_3$) and 1.273 (t, J=7, ethyl-CH$_3$).

Anal. Calcd. for $C_{24}H_{34}N_2O_6$: C, 64.55; H, 7.67; N, 6.27. Found: C, 63.91, 63.97; H, 7.70, 7.76; N, 6.42, 6.38.

MS: $C_{24}H_{34}N_2O_6$ requires m/z 446.2416; found, 446.2397.

EXAMPLE 4

[N-(1R-Ethoxycarbonyl-3-phenylpropyl)-RS-alanyl]-S-pyroglutamic Acid, Trifluoroacetic Acid Salt (I: R=OH, m=2, R$_1$=Me, R$_2$=H, R$_3$=EtO; R$_4$=—(CH$_2$)$_2$C$_6$H$_5$; •CF$_3$CO$_2$H)

When the product of Example 3(D) is subjected to the procedure of Example 2, [N-(1R-ethoxycarbonyl-3-phenylpropyl)-RS-alanyl]-S-proglutamic acid, trifluoroacetic acid salt, is obtained.

EXAMPLE 5

Preparation of [N-(1S-Ethoxycarbonyl-3-phenylpropyl)-RS-alanyl]-S-pyroglutamic acid, Benzyl Ester (I: R=C$_6$H$_5$CH$_2$O; m=2; R$_1$=Me; R$_2$=H, R$_3$=EtO; R$_4$=—(CH$_2$)$_2$C$_6$H$_5$)

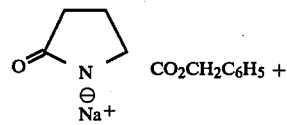

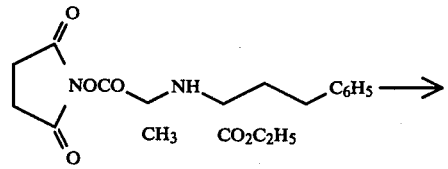

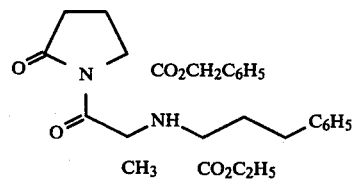

The procedure of Example 1(D) was applied to benzyl S-pyroglutamate (2.19 g, 10 mmole) in toluene (30 ml) using 60% sodium hydride (0.44 g, 11 mmole) to generate the anion. After 30 minutes, the mixture was treated with N-(1S-ethoxycarbonyl-3-phenylpropyl)-RS-alanine, N-succinimidyl ester, prepared as in Example 1(C) (3.76 g, 10 mmole) in toluene (20 ml). The mixture was allowed to react at 25° overnight, and the product isolated as described in Example 1(D), to provide 4.27 g (8.89 mmole, 89%) of crude product. Repetition of this experiment on 10- and 18.2-mmole scales gave yields of 84–89%. The two diastereomers of the product structure were observed as TLC spots, R$_f$0.90 (diastereomer A) and 0.85 (diastereomer B) (silica gel, 3:1 CH$_2$Cl$_2$:EtOAc). Flash chromatography of 4.29 g of crude product using the same absorbent acid solvent system gave 0.82 g of A and 2.70 g of (82% total recovery).

Purer samples of A and B were obtained by separation on silica gel using 85:15 CH$_2$Cl$_2$:EtOAc; separation of 33.74 g of crude ester by this method gave 4.95 g of A and 19.49 g of B.

Diastereomer A is a colorless oil with IR(CHCl$_3$): 3240, 1730 cm$^{-1}$.

MS: $C_{27}H_{33}N_2O_6$ (M+1) requires m/z 481.2338; found 481.2350.

[α]$_D^{25°}$ −16.8° (EtOH).

360 MHz NMR (CDCl$_3$): delta 4.150 (m, OCH$_2$, NCH); 3.423 (q, J=7, NCH); 3.327 (AB, J=6, NCH); 1.343 (d, J=6, alanine-CH$_3$); 1.226 (t, J=7, ethyl-CH$_3$).

Anal. Calcd. for $C_{27}H_{32}N_2O_6$: C, 67.48; H, 6.71; N, 5.83. Found: C, 71.05, 71.21; H, 7.49, 7.39; N, 4.45, 4.75.

Diastereomer B is also a colorless oil with IR(CHCl$_3$): 3340, 1745 cm$^{-1}$.

MS: $C_{27}H_{32}N_2O_6$ requires m/z 480.2260; found 480.2255.

[α]$_D^{25°}$ −53.9° (EtOH).

360 MHz NMR (CDCl$_3$): delta 4.767 (AB, J=4, NCH); 4.594 (q, J=7, NCH); 3.106 (AB, J=6, NCH); 4.128 (2q, J=7, OCH$_2$); 1.253 (d, J=7, alanine-CH$_3$); 1.250 (t, J=7, ethyl-CH$_3$).

Anal. Calcd. for $C_{27}H_{32}N_2O_6$: C, 67.48; H, 6.71; N, 5.83. Found: C, 67.51; H, 6.79; N, 5.77.

EXAMPLE 6

Preparation of [N-(1S-Ethoxycarbonyl-3-phenylpropyl)-RS-alanyl]-S-pyroglutamic acid, Hydrochloride (I: R=H, m=2; R$_1$=Me; R$_2$=H, R$_3$=EtO; R$_4$=—(CH$_2$)$_2$C$_6$H$_5$; •HCl)

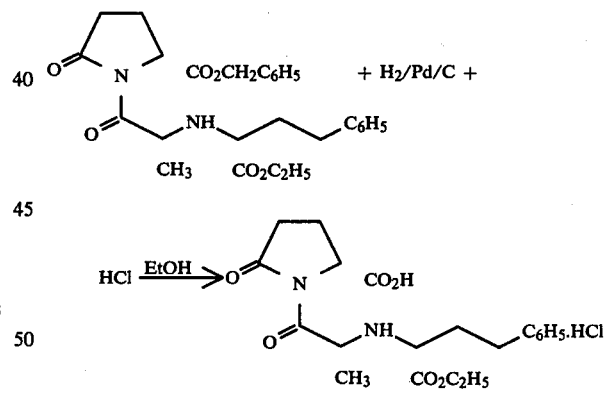

A mixture of the diastereomeric benzyl esters from the first paragraph of Example 5 (2.4 g, 5.0 mmole), ethanol (100 ml), concentrated hydrochloric acid (1 ml) and 5% palladium-on-carbon (0.5 g) was hydrogenated in a Parr shaker at 40 psig overnight. The mixture was filtered through Celite filter aid, and the filtrate evaporated to leave 2.10 g (4.9 mmole, 98%) of crude product as a gummy solid which lacked the delta 7.33 and 5.20 ppm signals of the benzyl group of the starting material. Its identity was confirmed by NMR and by its ability to prevent the conversion of angiotensin I to angiotensin II when administered sequentially and intravenously into rats. Repetition of the experiments gave a similar product which solidified on trituration and cooling with ether. This material was dried over P$_2$O$_5$ at 25°/0.1 mm and identified as a mixture of the diastereomeric acid products by the following criteria:

IR(CHCl$_3$): 1745, 1700 cm$^{-1}$.

$[\alpha]_D^{25°}$: −15.8° (EtOH).

Anal. Calcd. for C$_{20}$H$_{27}$N$_2$O$_6$Cl: C, 56.27; H, 6.37; N, 6.56. Found: C, 56.12; H, 6.52; N, 6.37.

The above reductive removal of the benzyl ester protecting group was carried out for each separate diastereomer A and B described in Example 5. The product obtained from 4.95 g (10.3 mmole) of the minor diastereomer, A, was a colorless hygroscopic solid material, yield 2.92 g (6.86 mmole, 67%) characterized as follows:

IR (KBr): 1745 cm$^{-1}$.

$[\alpha]_D^{25°}$: +23.9° (EtOH).

Anal. Calcd. for C$_{20}$H$_{26}$N$_2$O$_6$Cl: C, 56.27; H, 6.37; N, 6.56. Found: C, 56.92, 57.26; H, 7.26, 7.12; N, 4.80, 4.65.

The product obtained from 9.97 g (20.7 mmole) of the major diastereomer, B, was a colorless solid, yield 8.5 g (20.7 mmole, 100%) characterized as follows:

IR (KBr): 1741, 1700 cm$^{-1}$.

$[\alpha]_D^{25°}$: −30.7° (EtOH).

Anal. Calcd. for C$_{20}$H$_{26}$N$_2$O$_6$Cl: C, 56.27; H, 6.37; N, 6.56. Found: C, 56.32; H, 6.27; N, 6.35.

EXAMPLE 7

Preparation of
[N-(1S-Ethoxycarbonyl-3-phenylpropyl)-N-methyl-RS-alanyl]-S-pyroglutamic acid, Benzyl Ester (I: R=C$_6$H$_5$CH$_2$O; m=2, R$_1$=Me; R$_2$=Me; R$_3$=EtO; R$_4$=—(CH$_2$)$_2$C$_6$H$_5$).

A mixture of 1 g of the crude product diastereomeric esters from Example 5, paragraph 1, above, 37formaldehyde (10 ml) and 90% formic acid (10 ml) is stirred at reflux for 4 hours. The mixture is evaporated to leave the desired N-methyl compounds.

What is claimed is:

1. A process for preparing compounds of the formula:

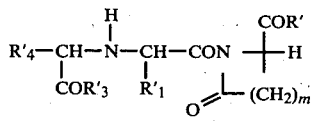

where
R' is OX, C$_1$-C$_4$ alkoxy or benzyloxy;
R$_1$' is H, CH$_3$, C$_2$H$_5$, CF$_3$, isobutyl, isoamyl, —(CH$_2$)$_n$NR$_5$—X$^1$ or —(CH$_2$)$_p$NH—C(=NH)NH—X$^2$;
R$_3$' is OX$^3$, C$_1$-C$_4$ alkoxy or benzyloxy;
R$_4$' is C$_1$-C$_{10}$ alkyl, —(CH$_2$)$_q$C$_6$H$_5$ or —(CH$_2$)$_r$NH—X$^4$;
R$_5$ is H or C$_1$-C$_4$ alkyl;
m is 2, 3 or 4;
n is an integer from 1-6;
p is an integer from 1-6;
q is an integer from 0-6;
r is an integer from 1-6; and
X, X$^1$, X$^2$, X$^3$ and X$^4$ are protective groups;
consisting essentially of coupling an anion of the formula

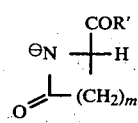

with an amino-diacid of the formula

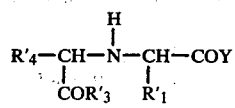

where Y is a carboxyl-activating group.

2. A process according to claim 1 where Y is N-succinimidyloxy.

3. A process for preparing compounds of the formula

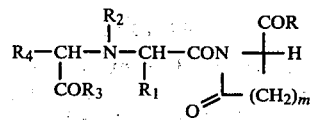

where
R and R$_3$ are independently OH, C$_1$-C$_4$ alkoxy or C$_6$H$_5$CH$_2$O;
R$_1$ is H, CH$_3$, C$_2$H$_5$, CF$_3$, isobutyl, isoamyl, —(CH$_2$)$_n$NHR$_5$ or

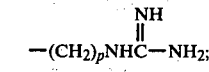

R$_2$ is H or CH$_3$;
R$_4$ is C$_1$-C$_{10}$ alkyl, —(CH$_2$)$_q$C$_6$H$_5$ or —(CH$_2$)$_r$NH$_2$;
R$_5$ is H or C$_1$-C$_4$ alkyl;
m is 2, 3 or 4;
n is an integer from 1-6;
p is an integer from 1-6;
q is an integer from 0-6; and
r is an integer from 1-6;
consisting essentially of
(a) coupling an anion of the formula

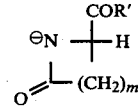

where R' is OX, C$_1$-C$_4$ alkoxy or benzyloxy, and m is as defined above;
with an amino-diacid of the formula

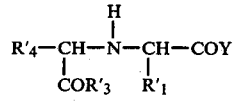

where
R$_1$' is H, CH$_3$, C$_2$H$_5$, CF$_3$, isobutyl, isoamyl, (CH$_2$)$_n$NR$_5$—X$^1$ or (CH$_2$)$_p$NH—C(=NH)NH—X$^2$;
R$_3$' is OX$^3$, C$_1$-C$_4$ alkoxy or benzyloxy;
R$_4$' is C$_1$-C$_{10}$ alkyl, —(CH$_2$)$_q$C$_6$H$_5$ or (CH$_2$)$_r$NH—X$^4$;
R$_5$, n, p, q and r are as defined above;
X, X$^1$, X$^2$, X$^3$ and X$^4$ are protective groups; and
Y is a carboxyl-activating group;
to prepare a compound where R$_2$=H;
(b) optionally methylating the product of step (a) to prepare a compound where R$_2$=CH$_3$; and
(c) removing the necessary protective groups to prepare the desired product.

4. A process according to claim 3 where Y is N-succinimidyloxy.

* * * * *

UNITED STATES PATENT AND TRADEMARK OFFICE
CERTIFICATE OF CORRECTION

PATENT NO. : 4,439,364             Page 1 of 5
DATED : MARCH 27, 1984
INVENTOR(S) : ALEXANDER L. JOHNSON It is certified that error appears in the above-identified patent and that said Letters Patent is hereby corrected as shown below:

Column 4, lines 1 to 10, formula should read:

Column 4, lines 29 to 38, formula should read:

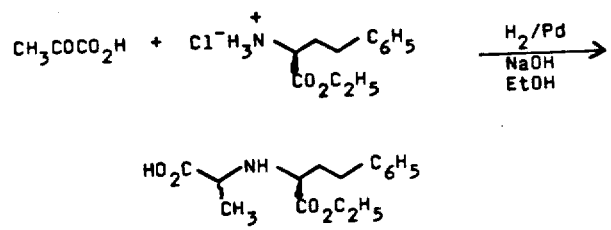

Column 5, lines 1 to 15, formula should read:

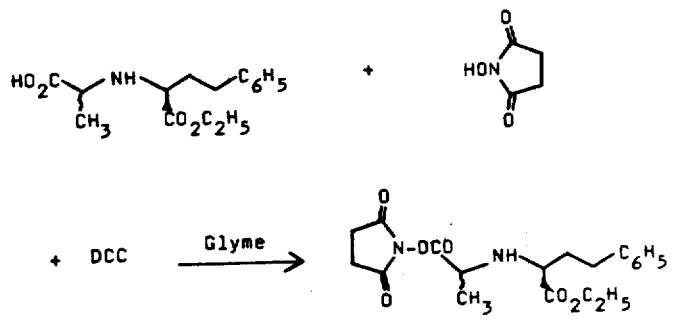

UNITED STATES PATENT AND TRADEMARK OFFICE
CERTIFICATE OF CORRECTION

PATENT NO. : 4,439,364

DATED : MARCH 27, 1984

INVENTOR(S) : ALEXANDER L. JOHNSON

It is certified that error appears in the above-identified patent and that said Letters Patent is hereby corrected as shown below:

Column 5, lines 37 to 58, formula should read:

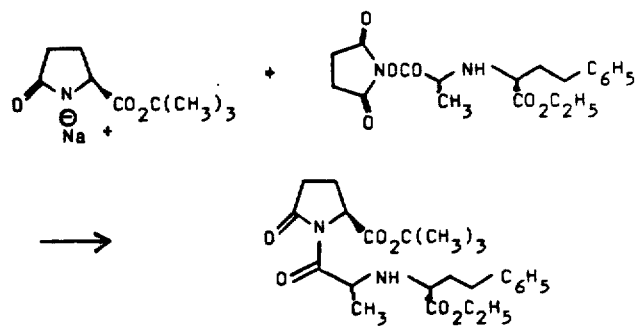

Column 6, lines 16 to 32, formula should read:

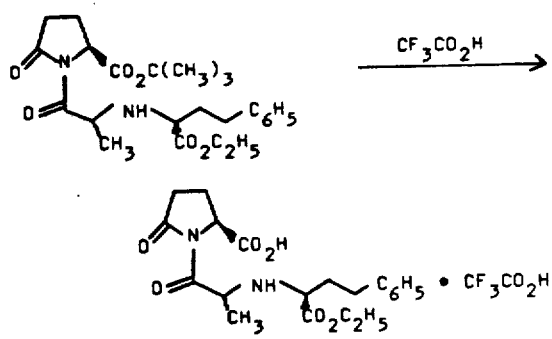

UNITED STATES PATENT AND TRADEMARK OFFICE
CERTIFICATE OF CORRECTION

PATENT NO. : 4,439,364
DATED : MARCH 27, 1984
INVENTOR(S) : ALEXANDER L. JOHNSON

It is certified that error appears in the above-identified patent and that said Letters Patent is hereby corrected as shown below:

Column 6, lines 50 to 57, formula should read:

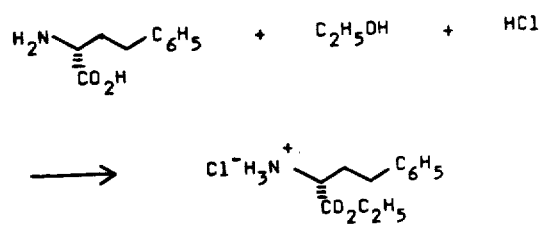

Column 7, lines 5 to 13, formula should read:

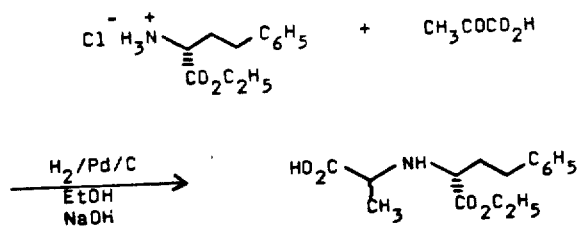

Column 7, lines 53 to 69, formula should read:

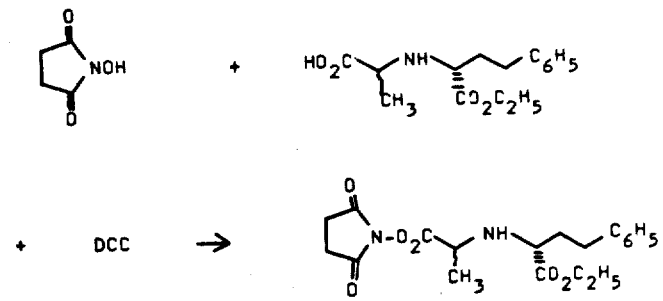

UNITED STATES PATENT AND TRADEMARK OFFICE
CERTIFICATE OF CORRECTION

PATENT NO. : 4,439,364

DATED : MARCH 27, 1984

INVENTOR(S) : ALEXANDER L. JOHNSON

It is certified that error appears in the above-identified patent and that said Letters Patent is hereby corrected as shown below:

Column 8, lines 24 to 43, formula should read:

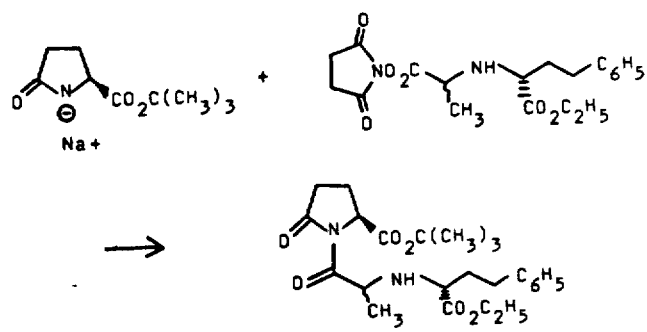

Column 9, lines 30 to 52, formula should read:

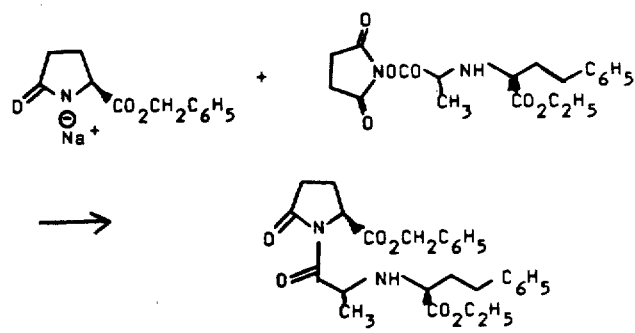

UNITED STATES PATENT AND TRADEMARK OFFICE
CERTIFICATE OF CORRECTION

PATENT NO. : 4,439,364

DATED : MARCH 27, 1984

INVENTOR(S) : ALEXANDER L. JOHNSON

It is certified that error appears in the above-identified patent and that said Letters Patent is hereby corrected as shown below:

Column 10, lines 37 to 53, formula should read:

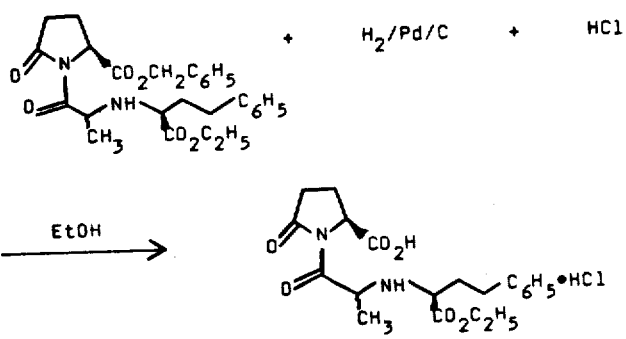

Signed and Sealed this

Ninth Day of October 1984

[SEAL]

Attest:

Attesting Officer

GERALD J. MOSSINGHOFF

Commissioner of Patents and Trademarks